United States Patent [19]

Pheulpin

[11] 3,955,719

[45] May 11, 1976

[54] CONICALLY WALLED SYRINGE PROVIDING A PROGRESSIVELY TIGHTER PISTON FIT

[76] Inventor: Jean Pheulpin, Avenue du Theatre 7, CH 1000 Lausanne, Switzerland

[22] Filed: Jan. 25, 1974

[21] Appl. No.: 436,668

[30] Foreign Application Priority Data
Jan. 30, 1973 Switzerland.......................... 1262/73

[52] U.S. Cl. ................................................ 222/386
[51] Int. Cl.² ......................................... G01F 11/00
[58] Field of Search ................ 128/261, 235, 218 P; 222/386, 390

[56] References Cited
UNITED STATES PATENTS

| | | | |
|---|---|---|---|
| 2,847,011 | 8/1958 | Jones ........................... | 128/235 UX |
| 3,189,231 | 6/1965 | Kibbel, Jr. et al. ............. | 222/386 X |
| 3,354,882 | 11/1967 | Coanda .......................... | 128/218 P |
| 3,537,605 | 11/1970 | Solowey .......................... | 222/386 X |
| 3,667,652 | 6/1972 | Morane et al. .................. | 222/386 X |

FOREIGN PATENTS OR APPLICATIONS

| | | | |
|---|---|---|---|
| 111,666 | 11/1925 | Switzerland ..................... | 128/218 P |

*Primary Examiner*—Robert B. Reeves
*Assistant Examiner*—Norman L. Stack, Jr.
*Attorney, Agent, or Firm*—Griffin, Branigan and Butler

[57] ABSTRACT

A syringe, such as used in dentistry to inject dental products, e.g. injection masses as so-called composites, cements, medicated pastes and the like into cavities. The syringe comprises a hollow cylinder, a piston axially movable in the cylinder, and a reservoir for the product to be injected. The piston fits into the reservoir which has at its front end a nozzle projecting out of the cylinder and at its back end an opening to receive the piston. At its front end the cylinder has a reduced inside diameter, so as to provide an abutment for the reservoir. The piston is removable from the cylinder so as to permit insertion of the piston into the back end of the reservoir, whereupon the piston with the reservoir attached to it can be inserted into the back end of the cylinder. Pressure on the piston forces the piston into the reservoir, so as to press the injection mass out of the nozzle of the reservoir. The use of a transparent material for the cylinder and the reservoir permits easy observation of the contents of the reservoir.

7 Claims, 7 Drawing Figures

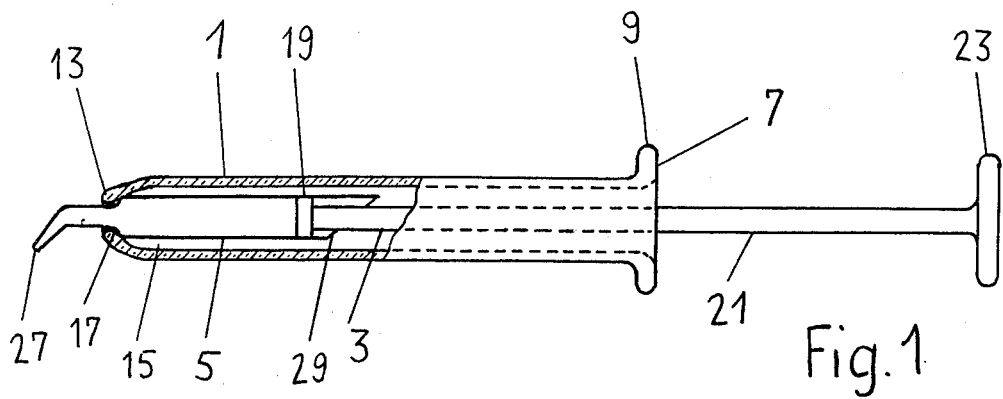
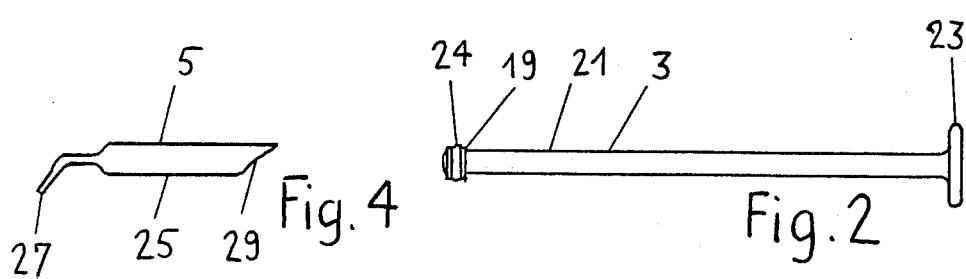
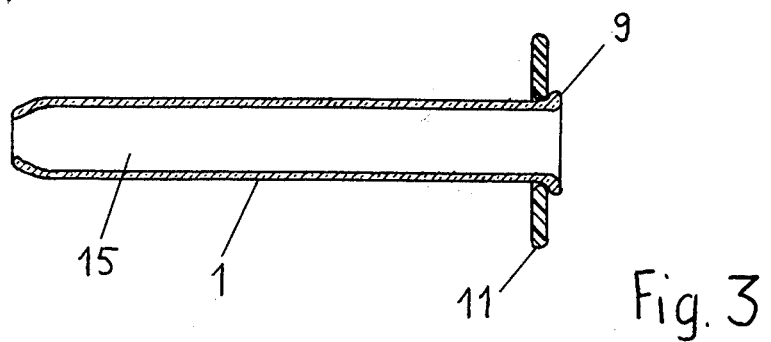

CONICALLY WALLED SYRINGE PROVIDING A PROGRESSIVELY TIGHTER PISTON FIT

BACKGROUND OF THE INVENTION

The present invention concerns a syringe for injecting an injection mass into a cavity or the like and comprising a hollow cylinder having a bore, a piston axially movable in said bore, and a reservoir for the injection mass, said cylinder having an opening for insertion of said reservoir, and said reservoir having at its front end a nozzle projecting out of the cylinder and at its back end an opening to receive the piston.

Syringes of this kind have heretofor been provided with a lateral opening for the insertion of a tubular reservoir made of plastic material and having at its front end a nozzle. Prior to its insertion the reservoir has to be filled with the injection mass by means of a spatula and then be closed with a plug to provide proper sealing.

After use of the prior art syringe, the disposable reservoir can be removed by pulling back the piston, whereupon the back end of the reservoir hits an abutment, so that the reservoir is stripped off from the piston to be thrown away.

As on the prior art device a lateral opening is required, the cylinder must be made of a sufficiently strong and machinable material, such as a stainless steel tube. Because it is necessary to provide retaining means at the front end of the stainless steel cylinder to receive the reservoir and stripping means behind the lateral opening, the manufacturing cost of the syringe is relatively high. It is also difficult to clean the syringe.

BRIEF DESCRIPTION OF THE INVENTION

It is an object of the present invention to provide a very simple syringe for injecting an injection mass into a cavity or the like.

It is a further object of the invention to provide a syringe where the cylinder can be of a material which can easily be cleaned and sterilized.

According to the present invention these objects are obtained in that the cylinder includes a bore and said bore constitutes, at the back end of the cylinder, the opening for insertion of said reservoir, that at the front end of the cylinder the bore is of reduced width to provide an abutment for the reservoir, and that the piston is removable from the cylinder so as to permit attachment of the reservoir to the piston by inserting the piston into the back end of the reservoir.

According to one embodiment of the invention the cylinder of the syringe consists of glass. Such a cylinder is easy to manufacture and is of sufficient strength, because no lateral opening is provided. When a transparent glass is used, the reservoir is easily visible after insertion.

According to a further embodiment the cylinder is provided with holding means consisting of a small flange at the back end of the cylinder and a flat ring retained by said flange. This provides for a very suitable construction of the syringe, particularily when the cylinder consists of glass, because on a glass tube a small flange can be formed with much less effort than a large flange. After putting a flat ring on the cylinder, this ring is retained by the flange and provides sufficient area to hold the syringe between two fingers when the thumb is pressing on the piston.

Other objects of the invention and its mode of operation will be better understood upon consideration of the following description and the accompanying drawing.

BRIEF DESCRIPTION OF THE DRAWING

FIG. 1 shows a partly sectional enlarged view of the syringe with the piston and the reservoir inserted and ready to use.

FIG. 2 shows a view of the piston.

FIG. 3 shows a somewhat enlarged view of a different embodiment of the cylinder.

FIG. 4 shows a cross-section through the reservoir.

DESCRIPTION OF PREFERRED EMBODIMENTS

Figure 5:
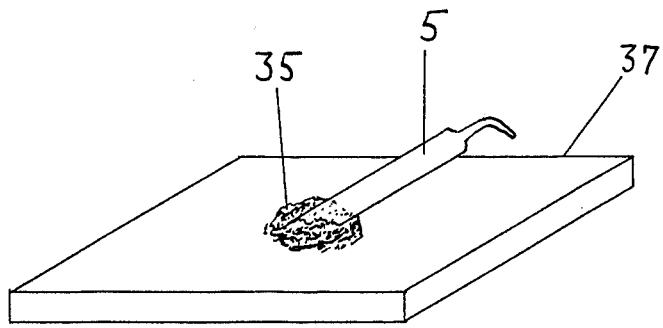
FIG. 5 shows the filling of the reservoir.

In a preferred embodiment of the invention illustrated in FIG. 1, the syringe comprises a cylinder 1, a piston 3, and a reservoir 5.

The cylinder 1, which is preferably of glass, particularily a heat resistant glass such as available under the trade name "Pyrex", comprises at its back end 7 holding means in form of a flange 9. In another embodiment shown in FIG. 3, only a small flange 9 is provided which serves as retaining means for a flat ring 11 of e.g. plastic material.

At the front end 13 of the cylinder the bore 15 is of narrower cross-section, so as to form an abutment 17 for the reservoir 5. The piston 3, which may consist of a suitable plastic material, has at one end a head 19 for insertion into the reservoir 5 and a piston stem 21 provided with a pusher 23 at its other end. At the head 19 a piston ring 24 (FIG. 2) of a suitable sealing material may be provided. The piston 3 may consist of a plastic material.

The reservoir 5, as shown in FIG. 4, consists preferably of a somewhat elastic or stretchable plastic material. It has the form of a thin walled tubular part 25 having at its front end a nozzle 27. At its back end the wall of the reservoir terminates in a plane which lies at a substantial angle with respect to a plane normal to the axis of the reservoir, thus providing a large opening 29 for the insertion of the injection mass.

While it is not evident from the drawing, the tubular part 25 of the reservoir 5 is slightly conical, so that the cross-section of the tubular part 25 is wider at the opening 29 than on the side comprising the nozzle 27. The dimensions are preferable chosen in such a way that the head 19 of the piston 3 can easily be inserted into the opening 29, but then sits tightly in the tubular part 25, so that further insertion causes expansion of the tubular part 25. This is easily possible if the wall of the tubular part 25 is of a somewhat elastic or stretchable material. In this way a very tight sealing is obtained between head 19 of the piston and the reservoir 5, even if no sealing ring 24 (FIG. 2) is provided.

Figure 6:
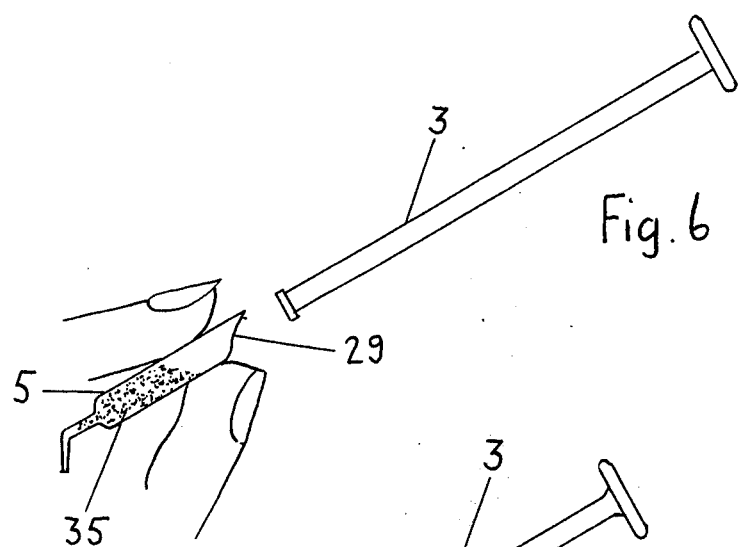
FIG. 6 shows the insertion of the piston into the reservoir.
Figure 7:
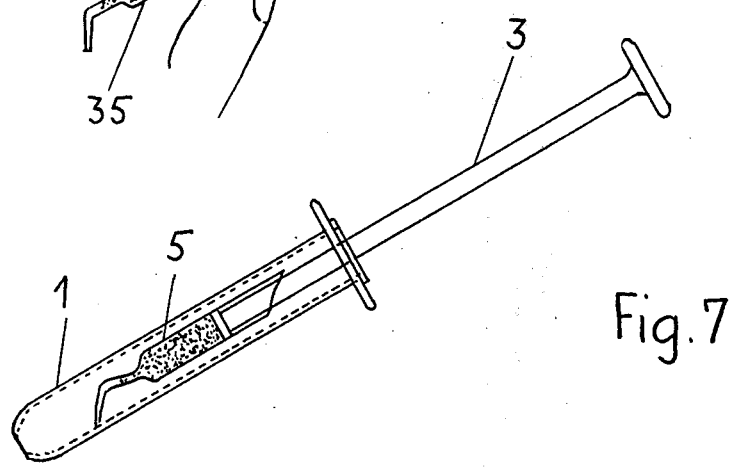
FIG. 7 shows the insertion of the piston on the attached reservoir into the cylinder.

The operation of the syringe will now be described with reference to FIGS. 5 to 7. As FIG. 5 shows, the reservoir 5 is filled by pressing it repeatedly with its opening 29 into the injection mass 35 prepared on a pad 37. The piston 3 is then inserted into the opening 29 (FIG. 6), whereupon the piston 3 together with the reservoir 5 is inserted into the tube 1 (FIG. 7). When fully inserted, the reservoir 5 and the piston 3 are in the position substantially as shown in FIG. 1. When used for the purposes of dentistry, the syringe is now ready to inject the injection mass into the cavity of a tooth. However, in addition to use in dentistry, the syringe may also be used for other applications. Therefore, as used in this specification and in the appended claims the term injection mass applies to any mass of material which may be loaded into the reservoir 5 through the opening 29 and ejected from the reservoir through the nozzle 27.

After use, the piston 3 with the empty reservoir 5 may be withdrawn from the cylinder 1, whereupon the reservoir 5 may be easily stripped from the piston 3 and discarded.

What I claim:

1. A syringe for injecting a material into a cavity or the like, said syringe comprising:
   a cylindrical tube having first and second ends,
   said first end being open and said second end being constricted;
   a generally tubularly walled reservoir for receiving the material to be injected, said reservoir having a first end with a nozzle thereon and an open second end,
   said reservoir being of such size as to be inserted nozzle end first into the open of said cylindrical tube and moved through said tube to said constricted end whereby said nozzle protrudes through said constricted end; and,
   a piston axially movable in the cylindrical tube and capable of being received into the open end of said reservoir, said piston forming a sliding seal with the wall of said reservoir whereby material in said reservoir is pushed toward said nozzle end as the piston is moved into said reservoir;
   the wall of said reservoir being conically shaped and made of a slightly stretchable material to provide an increasingly tighter sliding seal with said piston as the piston is moved toward said nozzle end.

2. A syringe for injecting a material into a cavity or the like, said syringe comprising:
   a cylindrical tube having first and second ends,
   said first end being open and said second end being constricted;
   a generally tubularly walled reservoir for receiving the material to be injected, said reservoir having a first end with a nozzle thereon and an open second end,
   said reservoir being of such size as to be inserted nozzle end first into the open end of said cylindrical tube once it has received said material to be injected and moved through said tube to said constricted end whereby said nozzle protrudes through said constricted end; and,
   a piston axially movable in the cylindrical tube and capable of being received into the open end of said reservoir, said piston forming a sliding seal with the wall of said reservoir whereby material in said reservoir is pushed toward said nozzle end as the piston is moved into said reservoir, said reservoir being slightly conically shaped to provide a progressively tighter fit with said piston as the piston moves into said reservoir from its open end;
   the wall of said reservoir at said open end terminating in a plane that lies at a substantial angle whereby the cross-sectional area of the internal bore of said reservoir is greater than the cross-sectional area of the internal bore of said reservoir.

3. A syringe as claimed in claim 2 wherein the walls of said reservoir are made of a stretchable plastic material.

4. A syringe as claimed in claim 3 wherein the internal bore of the tubular reservoir is of equal or smaller diameter than said piston except for a section near the open end where the piston is inserted into the reservoir.

5. A syringe as claimed in claim 3 wherein said reservoir and said cylinderical tube are made of transparent materials.

6. A syringe as claimed in claim 5 wherein said cylindrical tube is made of glass.

7. A syringe as claimed in claim 2 wherein said cylindrical tube is provided with a holding means thereon near its open end.

* * * * *